United States Patent [19]

Wellbrock

[11] 4,324,911
[45] Apr. 13, 1982

[54] PROCESS FOR THE CONTINUOUS PREPARATION OF DIACETYL ETHYLENE DIAMINE

[75] Inventor: Werner Wellbrock, Bad Soden am Taunus, Fed. Rep. of Germany

[73] Assignee: Hoechst Aktiengesellschaft, Frankfurt, Fed. Rep. of Germany

[21] Appl. No.: 194,751

[22] Filed: Oct. 7, 1980

[30] Foreign Application Priority Data

Oct. 10, 1979 [DE] Fed. Rep. of Germany ....... 2941023

[51] Int. Cl.³ ............................................. C07C 102/04
[52] U.S. Cl. ..................................... 564/141; 564/216
[58] Field of Search ......................... 564/141, 216, 159

[56] References Cited

U.S. PATENT DOCUMENTS 615,829 12/1898 Fehrlin ................................ 564/141
3,674,851 7/1972 Senoo et al. ........................ 564/141

FOREIGN PATENT DOCUMENTS 48-16895 5/1973 Japan .................................. 564/141
1335204 10/1973 United Kingdom ................ 564/141
1383583 2/1975 United Kingdom ................ 564/141

*Primary Examiner*—John Doll
*Attorney, Agent, or Firm*—Connolly and Hutz

[57] ABSTRACT

A process for the continuous preparation of diacetyl ethylene diamine, which comprises allowing a mixture of ethylene diamine and acetic acid to react in a low-temperature zone at a temperature of about 80° to 140° C., completing the reaction of the mixture in a subsequent high-temperature zone of from about 140° to 215° C., discharging the diacetyl ethylene diamine obtained at the end of the high-temperature zone and stripping the reaction water in countercurrent flow by an inert gas at a point located between the low-temperature and the high-temperature zone.

1 Claim, No Drawings

PROCESS FOR THE CONTINUOUS PREPARATION OF DIACETYL ETHYLENE DIAMINE

Diacetyl ethylene diamine (DAED) is generally prepared as intermediate product for tetraacetyl ethylene diamine (TAED), which latter is obtained therefrom by further acetylation. Tetraacetyl ethylene diamine is particularly important as bleaching activator in various low-temperature washing powders. A quasicontinuous cascade process for the manufacture of diacetyl ethylene diamine from acetic acid and ethylene diamine is described in German Offenlegungsschrift No. 2,118,282. According to the description in the example of this reference the process proceeds at least in two steps. Excess acetic acid is required for carrying out the column process described on page 2 of said reference. The space-time yield of both variants depends on the physico-technical conditions applied, which latter are a determinant factor for the velocity of the distillative removal of the reaction water obtained from the reaction zone. It is moreover difficult in this process to remove the reaction water quantitatively, which is necessary for a high yield for the further processing yielding TAED. The residual water content, which results in a destruction of acetic acid anhydride in the further processing yielding TAED is said to be about 1%.

A new process for the completely continuous preparation of diacetyl ethylene diamine has now been found which comprises allowing a mixture of ethylene diamine and acetic acid to react for some time in a low-temperature zone of about 80° to 140° C., completing the reaction of the mixture in a subsequent high-temperature zone of from about 140° to 215° C., preferably of from 160° to 180° C., discharging the diacetyl ethylene diamine obtained continuously at the end of the high-temperature zone, leading the reaction water obtained, while being formed, in countercurrent flow with an inert gas at a point located between the low-temperature and high-temperature zone to a fractionating column, preferably submitting the reaction water to a fractional distillation and recycling the reacting components separated by fractionation to the high-temperature zone.

The advantage of the process of the invention, as compared with the process disclosed in German Offenlegungsschrift No. 2,118,282 is that the reaction water obtained as water vapor need not pass in countercurrent flow acetic acid and ethylene diamine introduced as starting compounds, since a preliminary reaction has taken place in the low-temperature zone. It is only in this way that a stripping of the reaction water by means of an inert gas is possible so that the inert gas leaving the reactor and which is charged with steam is not charged with the starting compounds in countercurrent flow. It is therefore possible to obtain DAED prepared in the described manner practically quantitatively from the starting compounds with a residual water content smaller than 0.1%, that means, at least 10 times lower than that specified in said Offenlegungsschrift.

An apparatus suitable for carrying out the process of the invention is illustrated, by way of example, in schematical view in the accompanying drawing. This apparatus substantially consists of two packed columns (1) and (3), that are heatable or coolable, two heating zones (2) and (4) subsequent to columns (1) and (3), respectively, and of fractionating column (5). A mixture of acetic acid and ethylene diamine is fed via line (6) to the first packed column (1) which is heated to a temperature of from about 80° to 140° C., preferably about 90° C. This column is designated as low-temperature zone and acts as first reactor. The ratio of acetic acid to ethylene diamine is 2:1. An excess of acetic acid is not harmful, but not necessary either. Both starting components may be used in anhydrous form or as aqueous solutions.

The first packed column (1) is connected with heating zone (2) where the reaction mixture leaving column (1) is heated to a temperature of about 140° to 215° C. Next, the reaction mixture passes to the second packed column (3) connected with heating zone (4). In this heating zone the reaction mixture is kept at said temperature of 140° to 215° C. to complete its reaction. This latter heating zone may be connected, if desired, with further units consisting of a packed column and a heating zone of the same type as the above-disclosed.

The diacetyl ethylene diamine obtained is discharged continuously at the end of the last heating zone via line (7). The heating zones are preferably designed as zone heatings with forced circulation, in which the reaction mixture passes along the exterior and inner area of the heating means.

An inert gas, preferably nitrogen, is introduced into the zone having a temperature of from 140° to 215° C., hear named high-temperature zone, via line (8). The water formed during the reaction is stripped by means of this inert gas via line (9) located between the low-temperature and the high-temperature zone, together with possible intermediates such as monoacetyl ethylene diamine and is conveyed preferably to fractionating column (5), where it is submitted to fractional distillation. The water obtained in this fractionating column is discharged via line (10) and the residue is recycled to the high-temperature zone via line (11). The inert gas escapes via line (12) at the top of the fractionating column. The residence time of the reaction mixture in this apparatus varies from about 3 to 15, preferably 5 to 6, minutes.

The process according to the invention is superior over the process described in German Offenlegungsschrift No. 2,118,282 in that an excess reaction component is not required—although permitted—in this stepless continuous process and that therefore acetic acid and ethylene diamine can be used in a stoichiometrical ratio and finally in that the residence time of the product, as compared to that of the cascade connected system of the prior art, can be reduced to some minutes only.

In this way it has been possible to modify the distillative removal of the reaction water, which is the determinant factor for the velocity in the cascade process in a manner such that not the conversion rate hitherto determined by the distillation is reduced to the actual reaction rate. The reaction water obtained is evaporated in statu nascendi owing to the great area present during the reaction and is immediately stripped out of the reaction zone by the inert gas current. Therefore the removal of the reaction water is no longer determinant for the reaction rate like in the described cascade process so that the space-time yield is increased by about 5 to 10 times.

The invention is illustrated by the following example:

EXAMPLE

A mixture of 42 kg of acetic acid and of 21 kg of ethylene diamine, per hour, is fed to the first packed column (1), kept at a temperature of 90° C., of an apparatus as shown schematically in the accompanying drawing. The reaction mixture passes then to the high-temperature zone heated to 180° C., which consists of a first heating zone (2), a second packed column (3) and a second heating zone (9). Both packed column have a length of 1,000 mm and a width of 150 mm. The heating area in the first heating zone is 0.2 m² and in the second heating zone 0.4 m². Nitrogen is introduced continuously at a rate of about 50 l/h via line (8) located between packed column (3) and heating zone (4) and the reaction water obtained is stripped via line (9). The reaction water is subjected to a fractional distillation in fractionating column (5) and the residue is recycled to the high-temperature zone via line (11). At the end of the second heating zone there are obtained per hour 5 kg of pure diacetyl ethylene diamine.

What is claimed is:

1. A process for the continuous preparation of diacetyl ethylene diamine, which comprises allowing a mixture of ethylene diamine and acetic acid to react in a low-temperature zone at a temperature of about 80° to 140° C., completing the reaction of the mixture in a subsequent high-temperature zone of from about 160° to 215° C., discharging the diacetyl ethylene diamine obtained at the end of the high-temperature zone and stripping the reaction water in counter-current flow by an inert gas at a point located between the low-temperature and the high-temperature zone.

* * * * *